US007963979B2

(12) United States Patent
Phillips et al.

(10) Patent No.: US 7,963,979 B2
(45) Date of Patent: Jun. 21, 2011

(54) PROVISIONAL BONE PLATE

(75) Inventors: Mark Phillips, Warsaw, IN (US); Mark Bryant, Auburn, IN (US); Bradley T. Durcholz, Warsaw, IN (US); Krishnakant K. Merchant, Fort Wayne, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 146 days.

(21) Appl. No.: 12/402,167

(22) Filed: Mar. 11, 2009

(65) Prior Publication Data

US 2009/0171398 A1 Jul. 2, 2009

Related U.S. Application Data

(63) Continuation of application No. 10/324,471, filed on Dec. 20, 2002, now Pat. No. 7,736,365.

(51) Int. Cl.
*A61B 17/58* (2006.01)

(52) U.S. Cl. ...................................... 606/280

(58) Field of Classification Search .................. 606/280, 606/281, 298, 86 B, 71, 60, 293, 291, 289, 606/286, 247, 70, 902, 283
See application file for complete search history.

(56) References Cited

U.S. PATENT DOCUMENTS

| 3,748,778 | A | | 7/1973 | Ellis et al. | |
|---|---|---|---|---|---|
| 3,882,630 | A | | 5/1975 | Bianco | |
| 5,041,113 | A | * | 8/1991 | Biedermann et al. | 606/288 |
| 5,250,048 | A | * | 10/1993 | Gundolf | 606/297 |
| 5,752,958 | A | | 5/1998 | Wellisz | |
| 5,785,712 | A | * | 7/1998 | Runciman et al. | 606/283 |
| 5,938,662 | A | | 8/1999 | Rinner | |
| 6,096,040 | A | * | 8/2000 | Esser | 606/280 |
| 6,123,709 | A | | 9/2000 | Jones | |
| 6,206,882 | B1 | | 3/2001 | Cohen | |
| 6,364,881 | B1 | | 4/2002 | Apgar et al. | |
| 6,383,186 | B1 | * | 5/2002 | Michelson | 606/70 |
| 7,077,844 | B2 | * | 7/2006 | Michelson | 606/71 |

* cited by examiner

*Primary Examiner* — Pedro Philogene
(74) *Attorney, Agent, or Firm* — Baker & Daniels LLP

(57) ABSTRACT

A provisional bone plate formed of an implantable plastic and having a length corresponding to the longest bone plate in a particular family of bone plates. The provisional bone plate includes a head contoured to match the head of a particular bone as well as a shaft for placement adjacent the bone shaft. The provisional bone plate includes a plurality of circumferential notches surrounding the elongate body or shaft of the bone plate. The circumferential notches are substantially transverse to a longitudinal axis of the bone plate and define frangible portions of the bone plate which can be removed from the distal end thereof to alter the length of the provisional periarticular bone plate to correspond to the length of the various bone plates in a family of bone plates. The provisional bone plate is constructed of a biologically suitable plastic, is radiographic, and melts at a temperature less than 200° Fahrenheit.

10 Claims, 3 Drawing Sheets

PROVISIONAL BONE PLATE

CROSS-REFERENCE TO RELATED APPLICATIONS

This application is a Continuation of U.S. patent application Ser. No. 10/324,471, filed Dec. 20, 2002, now U.S. Pat. No. 7,736,365, the disclosure of which is hereby expressly incorporated by reference herein.

BACKGROUND OF THE INVENTION

1. Field of the Invention

The present invention relates to bone plates, and, more particularly, to a provisional bone plate for determining the appropriately sized bone plate for a particular application.

2. Description of the Related Art

It is known to utilize bone plates in osteosynthesis. For example, the periarticular plating system available from Zimmer, Inc. is useful in osteosynthesis of periarticular bones. Known bone plates are used to maintain discrete portions of a fractured or otherwise severed bone substantially stationary relative to one another to, e.g., reduce a fracture and facilitate healing of the bone.

Periarticular bones typically include a shaft with a head at either end. The heads of periarticular bones have an enlarged periphery relative to the periphery of the bone shaft to provide a larger load bearing surface at the bone end. Known bone plates attach to both the head and the shaft of the bone to maintain the head substantially stationary relative to the shaft. With this in mind, known bone plates include an elongate portion for attachment to the bone shaft, and a flared head portion for attachment to the bone head. The contour of a bone plate is made to match the contour of the bone to which it will be attached either before or during the implantation procedure. For example, the Zimmer periarticular plating system provides pre-countered bone plates for affixation to certain aspects of particular periarticular bones. Moreover, the Zimmer periarticular plating system provides a family of plates for each bone aspect, with each plate in a family having a different shaft length. Straight bone plates are utilized for traditional non-periarticular fractures When treating a bone fracture, a surgeon must choose a bone plate applicable to the fractured bone and to the particular bone aspect requiring osteosynthesis. Once the type of bone plate has been chosen, the appropriate size must next be chosen. A shorter bone plate may be more suitable in those instances where the fracture location is located close to the joint, and also when the extra length of plate to be implanted would necessitate a longer incision than may be necessary. Having a plate that is longer than required to treat the fracture in question is more expensive in terms of both plate expense and surgical time. To chose the ideal bone plate length, a surgeon will typically utilize a plate that is just long enough to bridge the fracture and provide fixation points on the shaft of the bone on either side of the fracture.

In the past, surgeons would open a bone plate from the appropriate family and place it against the bone to test for appropriate size. If the surgeon determined that a longer or shorter bone plate was required, then another bone plate would be removed from its packaging and placed against the bone. This procedure was repeated until an appropriately sized bone plate was chosen. Utilizing this trial and error procedure increases the costs of the surgical procedure because multiple bone plates must be purchased.

What is needed in the art is a provisional bone plate useful for choosing an appropriately sized implantable bone plate for reducing a fracture.

SUMMARY OF THE INVENTION

The present invention provides a provisional bone plate formed of an implantable material, e.g., plastic and having a length corresponding to the longest bone plate in a particular family of bone plates. For example, the provisional bone plate of the present invention may be adapted for choosing an appropriate proximal lateral tibial bone plate from a family of proximal lateral tibial bone plates having eight (8) different bone plate lengths, with each of the eight (8) bone plates having a head contoured to match the proximal lateral tibia. In this case, the provisional bone plate of the present invention includes a head contoured to fit the proximal lateral tibia and includes a shaft or elongate portion having a length corresponding to the longest of the proximal lateral tibial plates. Moreover, the provisional bone plate of the present invention includes a plurality of circumferential notches surrounding the elongate body of the bone plate and being substantially transverse to a longitudinal axis thereof. The notches define frangible portions of the bone plate which can be removed from the distal end thereof to alter the length of the provisional periarticular bone plate to correspond to every bone plate in the particular family of bone plates.

While described with reference to a provisional periarticular bone plate, the provisional bone plate of the present invention is usable with any bone plate family having variable size, including both right and left bone plates. The provisional bone plate of the present invention is in one exemplary embodiment constructed of a biologically suitable plastic, is radiographic, and meltable at a temperature less than 200° Fahrenheit. Moreover, the provisional bone plate of the present invention is constructed to avoid fracture at the notches or otherwise when dropped.

In use, the provisional bone plate of the present invention is placed adjacent to a fractured bone and tested for length. If the provisional plate is of suitable length, then the longest bone plate in the corresponding family of bone plates is chosen and secured to the fractured bone. If the provisional bone plate is too long, then the distal most frangible portion defined by the distal most notch may be removed from the bone plate by fracturing the provisional bone plate along the distal most notch. For the purposes of this document, proximal and distal are used with reference to the provisional bone plate with the head of the provisional bone plate being the proximal most point thereof. The length of the provisional bone plate can then again be checked and the process of fracturing the distal most frangible portion repeated as necessary until the provisional bone plate is the appropriate size for use with the fractured bone. The final bone plate may then be chosen according to the size of the provisional bone plate. To chose the ideal bone plate length, a surgeon will typically utilize a plate that is just long enough to bridge the fracture and provide fixation points on the shaft of the bone on either side of the fracture.

The invention, in one form thereof, comprises a provisional bone plate including an elongate body having a notch defining a frangible portion of the provisional bone plate.

The invention, in another form thereof, comprises a provisional bone plate having an elongate body and fracture means for defining frangible portions of the elongate body.

The invention, in a further form thereof, comprises a method of choosing one of a family of bone plates for securement to a bone. The method of this form of the present invention includes the steps of: providing a provisional bone plate including an elongate body having a plurality of notches defining a plurality of frangible portions of the provisional body plate; determining whether the elongate portion of the provisional bone plate is too long; fracturing the bone plate along the distal most notch and again determining whether the elongate portion of the provisional bone plate is too long; repeating the determining and fracturing steps until the provisional bone plate is no longer too long; and choosing an implantable bone plate corresponding to the size of the provisional bone plate after the last fracturing step.

Advantageously, the provisional periarticular bone plate of the present invention does not require the opening of multiple periarticular bone plates to determine the appropriately sized plate for affixation to a fractured bone.

Another advantage of the recent invention is that the provisional bone plate can be easily located in the body if misplaced due to its radiographic properties.

Yet another advantage of the provisional bone plate of the present invention is the fact that it cannot be accidentally steam autoclaved and used a second time because the melt temperature is less than the temperature achieved by a standard steam autoclave.

A further advantage of the present invention is the fact that the provisional bone plate resists fracture when dropped.

BRIEF DESCRIPTION OF THE DRAWINGS

The above-mentioned and other features and advantages of this invention, and the manner of attaining them, will become more apparent and the invention itself would be better understood by reference to the following description of an embodiment of the invention taken in conjunction with the accompanying drawings, wherein.

Figure 1:
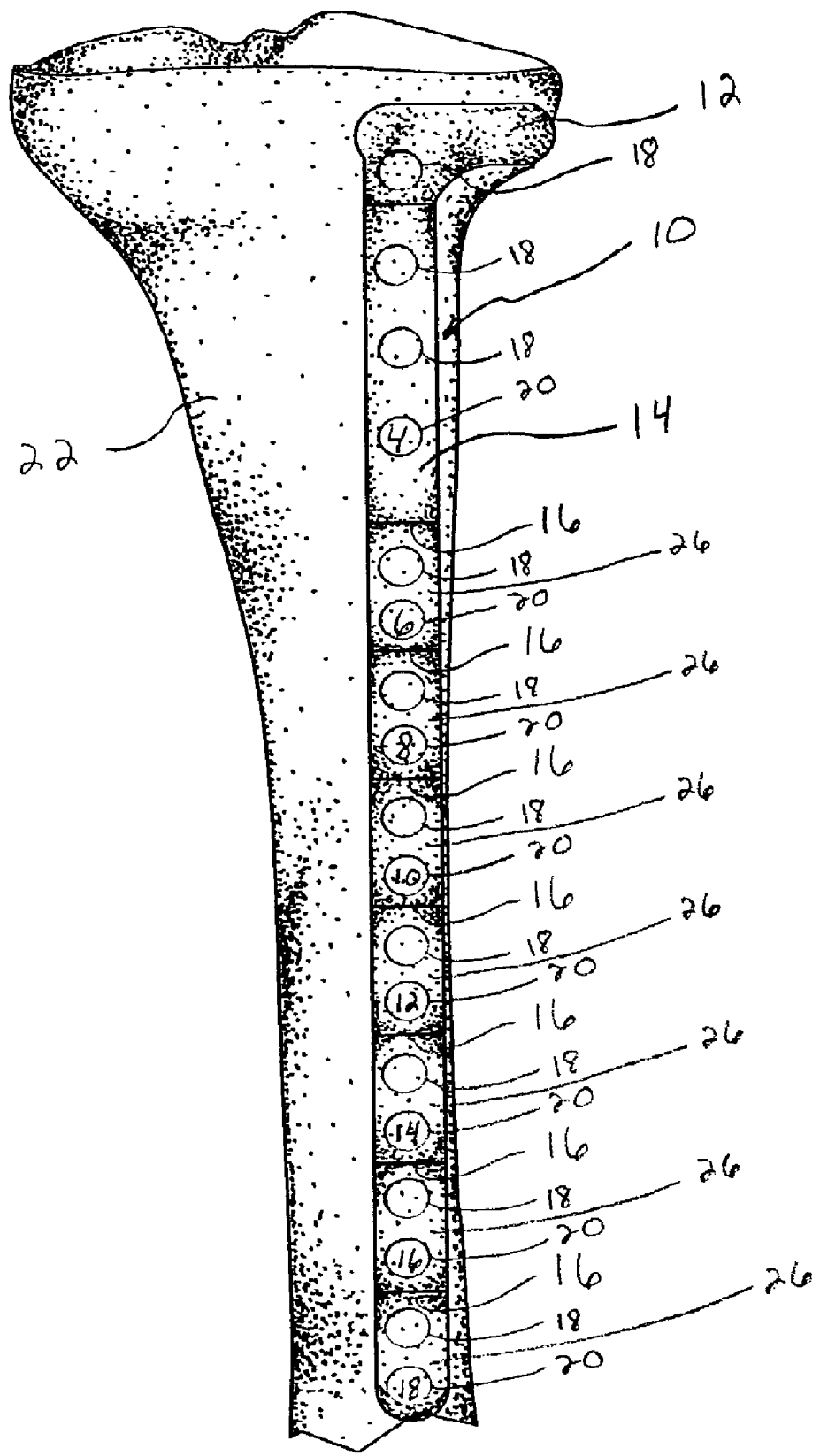
FIG. 1 is a perspective, fragmentary view of a provisional bone plate of the present invention positioned adjacent a tibia.

Corresponding reference characters indicate corresponding parts throughout the several views. Although the drawings represent an embodiment of the invention, the drawings are not necessarily to scale and certain features may be exaggerated to better illustrate and explain the invention. The exemplification set out herein illustrates an embodiment of the invention and such exemplification is not to be construed as limiting the scope of the invention in any manner.

DETAILED DESCRIPTION

Referring to the drawings and particularly to FIG. 1, there is illustrated provisional bone plate 10 positioned adjacent tibia 22. As illustrated in FIG. 1, provisional bone plate 10 includes head 12 and elongate body or shaft 14. As illustrated in FIG. 1, head 12 is anatomically contoured to fit the head of tibia 22 similar to the contouring of the final bone plate. Provisional bone plate 10 includes a plurality of hole markings 18, 20, with holding markings 20 including a size indicator. Hole markings 18, 20 replicate the screw hole apertures found in the corresponding implantable bone plate. Hole markings 20 include size indicators useful in determining plate size as will be further described herein below.

Figure 2:
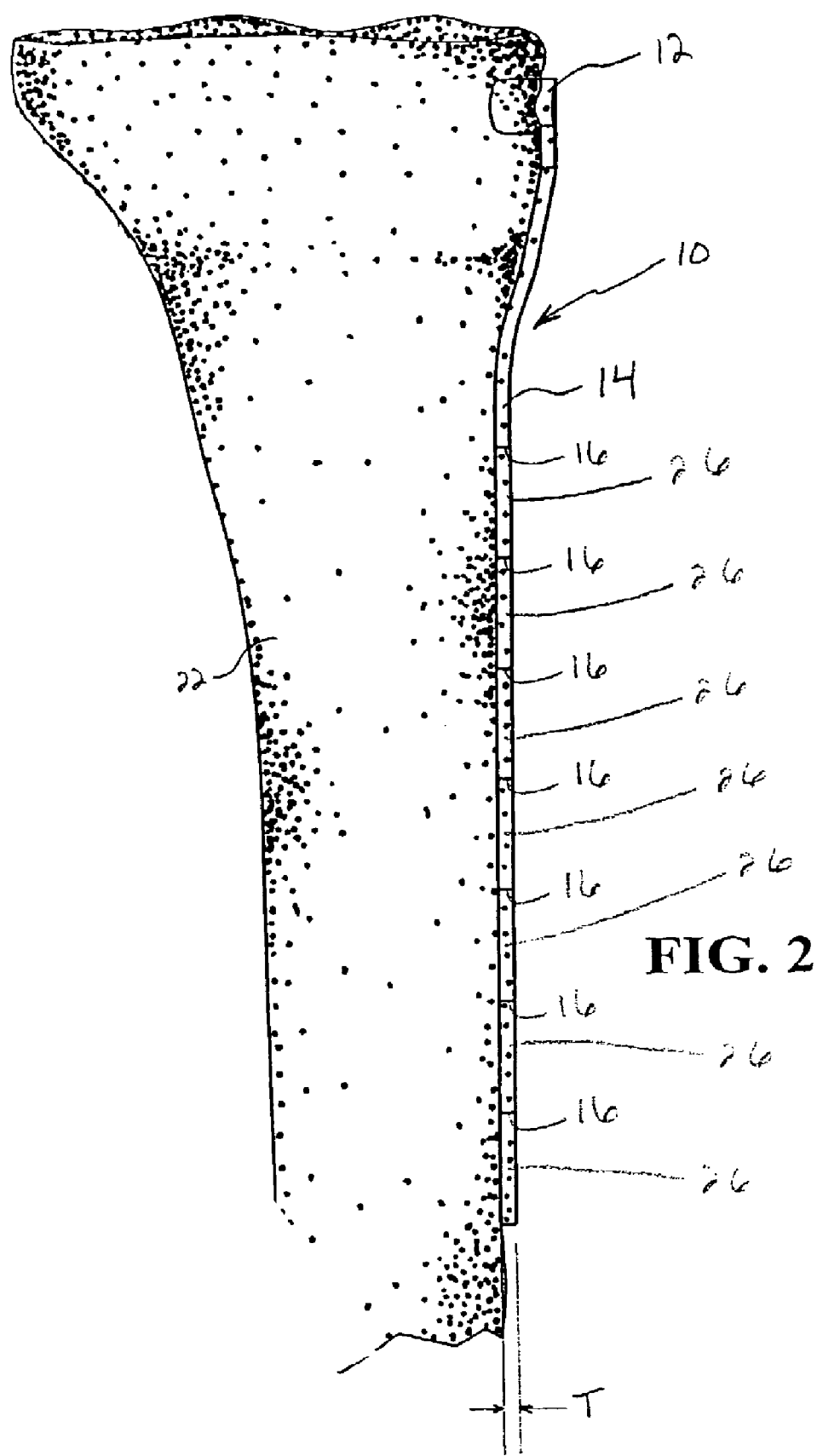
FIG. 2 is another perspective, fragmentary view of the provisional bone plate and tibia of FIG. 1.
Figure 3:
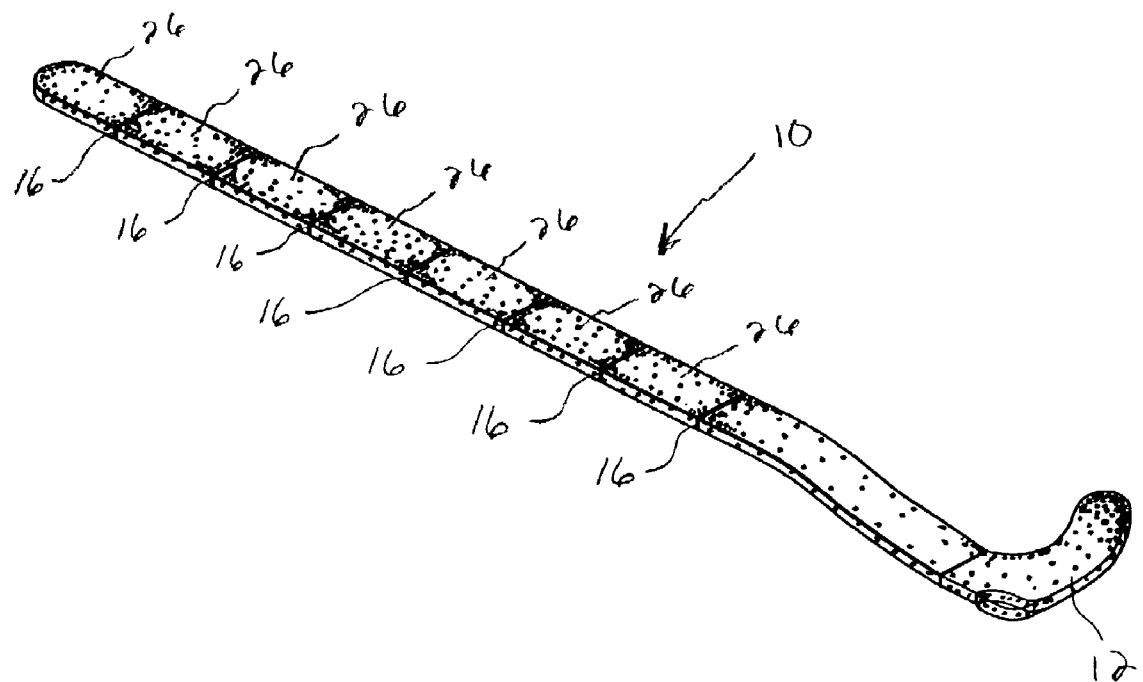
FIG. 3 is a perspective view of a provisional bone plate in accordance with the present invention.

As illustrated in FIGS. 1-3, provisional bone plate 10 includes a plurality of circumferential notches 16 defining a plurality of frangible portions 26. In one exemplary embodiment, circumferential notches 16 comprise V-shaped notches oriented substantially transverse to a longitudinal axis of elongate body 14 of provisional bone plate 10. Provisional bone plate 10 may be fractured along notches 16 to decrease the length of elongate body 14 of provisional bone plate 10. In one exemplary embodiment, notches 16 are V-shaped notches having a depth equal to 10-30% of the thickness T of provisional bone plate 10 as illustrated in FIG. 2. In another exemplary embodiment, circumferential notches 16 are V-shaped notches having a depth measuring 20% of the thickness T of provisional bone plate 10. Importantly, notches 16 are sufficiently deep whereby sufficient shear force applied to a notch (16), or bending force applied adjacent a notch (16) will cause provisional bone plate 10 to fracture at the notch (16). Provisional bone plate 10 will not, however, fracture if dropped. In one exemplary embodiment, notches 16 are V-shaped notches having a base measuring 0.025-0.30 inches and a depth measuring 0.021-0.021 inches. While described as having V-shaped notches to facilitate resizing thereof, "notch" is used as a general term in this document to indicate any scoring or other reduction in cross-section.

Hole markings 20 include size indicators operable to identify one of the bone plates in a particular family of plates. For the purposes of this document "family of plates" is used to indicate a group of plates contoured to match the particular aspect of a bone and having elongate portions of varying lengths for securement to the shaft of that bone. Hole markings 20 illustrated in FIG. 1 include a size indicator indicative of the number of shaft screw apertures found in the corresponding implantable bone plate. For example, the proximal most hole marking 20 includes the number 4 indicating four (4) screw apertures. This means that if provisional bone plate 10 is fractured along notch 16 positioned adjacent to hole marking 20 including the indicator 4, that the provisional bone plate will then be sized corresponding to the implantable periarticular bone plate of the appropriate family having four (4) screw apertures along its elongate portion or shaft. This is similarly true of subsequent hole markings having indicators 4, 6, 8, 10, 12, 14, 16, and 18. The size indicators of hole markings 20 may be indicative of other features of the individual plates of the family, including, e.g., shaft length.

Generally, provisional bone plate 10 is constructed from a biological suitable plastic such as, e.g., Acrylonitrile Butadiene Styrene (ABS), polystyrene, or Polymethylmethacrylate (PMMA). The plastic from which provisional bone plate 10 is formed sometimes includes a radiographic filler such as barium sulfate or titanium oxide to facilitate location of the provisional bone plate in the body if misplaced. In one exemplary embodiment, the radiographic filler comprises 10% of the material of construction. Color additives may be included to facilitate part identification. For example, a particular color may be used to identify a provisional bone plate adapted for use with a particular aspect of a particular bone. Advantageously, provisional bone plate 10 melts at less than the temperature achieved in a standard steam autoclave to prevent multiple uses. In construction, provisional bone plate 10 is injected molded from a material having the aforementioned characteristics and is thereafter gamma sterilized and placed in sterile packaging prior to use.

In use, provisional bone plate 10 is placed adjacent tibia 22 and tested for length as illustrated in FIGS. 1 and 2. If provisional bone plate 10 is of suitable length, then the longest bone plate in the corresponding family is chosen and secured to tibia 22. If provisional bone plate 10 is too long, then provisional bone plate 10 will be fractured along notch 16 positioned intermediate hole markings 20 having size indicators 16, 18. The length of provisional bone plate 10 is again checked and the process of fracturing the distal most frangible portion is repeated as necessary until the provisional bone plate is the appropriate size for use with tibia 22. Finally, the bone plate to be implanted is chosen according to the final size of provisional bone plate 10.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A bone plate system, comprising:
    a family of bone plates, comprising:
        a first bone plate having a first bone plate shaft and defining a first bone plate length; and
        a second bone plate having a second bone plate shaft and defining a second bone plate length, said first bone plate and said second bone plate both adapted for selective securement to a bone, said second bone plate length less than said first bone plate length, whereby said first bone plate and said second bone plate are adapted for the treatment of different fractures of the bone; and
    a provisional bone plate, comprising:
        an elongate body having a first end and a second end opposite the first end, the elongate body including a notch defining a frangible portion of the provisional bone plate, said provisional bone plate defining a first length from said first end to said second end, said first length corresponding to said first bone plate length, said provisional bone plate defining a second length from said first end to said notch, said second length corresponding to said second bone plate length, whereby said provisional bone plate can be positioned adjacent the bone to determine whether said first bone plate is appropriate for treating a fracture of the bone and whereby, with said provisional bone plate fractured at said notch and said frangible portion removed to form a fractured provisional bone plate, said fractured provisional bone plate can be positioned adjacent the bone to determine whether said second bone plate is appropriate for treating the fracture of the bone.

2. The bone plate system of claim 1, wherein said provisional bone plate further comprises a head contoured to substantially match a profile of a bone head of bone, said elongate body extending from said head.

3. The bone plate system of claim 1, wherein said first notch comprises a V-shaped notch.

4. The bone plate system of claim 1, wherein said first notch has a depth of about 10-30% of the thickness of said elongate body.

5. The bone plate system of claim 1, wherein said first notch has a depth of about 20% of the thickness of said elongate body.

6. The bone plate system of claim 1, wherein said provisional bone plate further comprises a plurality of hole markings formed on said elongate body.

7. The bone plate system of claim 1, wherein said provisional bone plate further comprises a plurality of size indicators positioned along said elongate body.

8. The bone plate system of claim 1, wherein said first notch is substantially transverse to a longitudinal axis of said elongate body.

9. The bone plate system of claim 1, wherein said elongate body of said provisional bone plate is formed from a plastic material having a melting point of less than two hundred degrees Fahrenheit.

10. The bone plate system of claim 1, said elongate body having a thickness and a circumference, wherein said notch comprises a circumferential notch formed about said circumference of said elongate body.

* * * * *